United States Patent [19]

Yoshida et al.

[11] Patent Number: 5,004,825

[45] Date of Patent: Apr. 2, 1991

[54] PROCESS FOR PREPARING DI(FLUOROALKYL CONTAINING GROUP-SUBSTITUTED ALKYL) PHOSPHATE SALT

[75] Inventors: Tutomu Yoshida; Shigeharu Iida, both of Osaka, Japan

[73] Assignee: Daikin Industries Ltd., Osaka, Japan

[21] Appl. No.: 381,324

[22] Filed: Jul. 18, 1989

Related U.S. Application Data

[63] Continuation-in-part of Ser. No. 184,673, Apr. 22, 1988, abandoned.

[30] Foreign Application Priority Data

Apr. 22, 1987 [JP] Japan .................... 62-100868

[51] Int. Cl.$^5$ .............................................. C07F 9/02
[52] U.S. Cl. .................................... 558/131; 558/204
[58] Field of Search ............................. 558/204, 131

[56] References Cited

U.S. PATENT DOCUMENTS

| | | | |
|---|---|---|---|
| 2,597,702 | 5/1952 | Benning | 558/204 |
| 3,096,207 | 7/1963 | Cohen | 558/204 |
| 4,145,382 | 3/1979 | Hayashi et al. | 558/204 |

FOREIGN PATENT DOCUMENTS

| | | |
|---|---|---|
| 2755530 | 6/1978 | Fed. Rep. of Germany . |
| 54-7776 | 10/1979 | Japan . |

OTHER PUBLICATIONS

Hayashi et al., Chem. Abst. 89-108132W (1978).
English Abstract of Japanese 60-64990, 8/85.
English Abstract of Japanese 56-25190, 5/81.
English Abstract of Japanese 52-65222, 9/77.

*Primary Examiner*—Cecilia Shen
*Attorney, Agent, or Firm*—Birch, Stewart, Kolasch & Birch

[57] ABSTRACT

A di(fluoroalkyl containing group-substituted alkyl) phosphate salt which is useful for a surface active agent, a water- and/or oil-repellent for fiber or paper or an oil resistant agent, can be prepared a process which comprises hydrolyzing a mono-sec.- or tert.-alkyl (di(-fluoroalkyl containing group-substituted alkyl) phosphate with a base.

10 Claims, No Drawings

PROCESS FOR PREPARING DI(FLUOROALKYL CONTAINING GROUP-SUBSTITUTED ALKYL) —SO₂, PHOSPHATE SALT

This is a continuation-in-part application of Ser. No. 07/184,673 filed on Apr. 22, 1988, now abandoned.

BACKGROUND OF THE INVENTION

1. Field of the Invention

The present invention relates to a process for preparing a di(fluoroalkyl containing group-substituted alkyl) phosphate salt.

The di(fluoroalkyl containing group-substituted alkyl) phosphate salt is useful as a surface active agent, a water- and/or oil-repellent for fiber or paper or an oil resistant agent.

2. Description of the Related Art

Processes for preparing fluoroalkyl containing group-substituted alkyl phosphate esters are disclosed in, for example, Japanese Patent Publications Nos. 7776/1979, 29875/1981 and 48158/1982 and Japanese Patent Kokai Publication No. 64990/1985.

However, the phosphate esters which are obtained by the above processes have wide distribution of composition which contains two or three of a monoalkyl ester, a dialkyl ester and a trialkyl ester. Of these three esters, the di(fluoroalkyl containing group-substituted alkyl) phosphate ester has the highest oil resistance, but is not produced in a high selectivity and contains relatively large amounts of monoalkyl and trialkyl esters. A yield of dialkyl esters is at most about 80% by weight, as described in Examples of Japanese Patent Publication No. 7776/1979. It is desired to increase the selectivity of dialkyl esters.

SUMMARY OF THE INVENTION

An object of the present invention is to provide a process for preparing a fluoroalkyl containing group-substituted alkyl phosphate ester by which a dialkyl ester is produced in a high selectivity.

This and other objects of the present invention are achieved by a process for preparing a di(fluoroalkyl containing group-substituted alkyl) phosphate salt which comprises hydrolyzing a mono-sec.- or tert.-alkyl di(fluoroalkyl containing group-substituted alkyl) phosphate with a base.

DETAILED DESCRIPTION OF THE INVENTION

Illustrative types of the di(fluoroalkyl containing group-substituted alkyl) phosphate salt produced by the process according to the present invention are of the formula:

$$[R_f-A^1{}_k-(CH_2)_m-O]_2PO-OA^2 \qquad (I)$$

wherein each $R_f$ is independently a perfluoroalkyl group or ω-hydroperfluoroalkyl group having 3 to 21 carbon atoms,
each $A^1$ is independently a divalent group which bonds $R_f$ to $-(CH_2)_m-$,
$A^2$ is an alkaline metal or an ammonium group which may be substituted with an alkyl and/or hydroxyalkyl group,
k is 0 or 1, and
m is an integer of 1 to 4.

$R_f$ in the formula (I) may be linear, branched, cyclic (for example, perfluorocyclohexyl) or combination thereof.

$A^1$ is, for example, $-O-$, $-)_3-O-$, $-S-$, $-(CH_2)_p-NR'-$, $-CH_2CH(OR')-$, $-CO-NR'-$ or $-SO_2-NR'$ in which R' is a hydrogen or an alkyl group having 1 to 5 carbon atoms and p is an integer of 1 to 6.

Specific examples of the di(fluoroalkyl containing group-substituted alkyl) phosphate salt of the formula (I) are:

$(C_4F_9CH_2CH_2O)_2POONH_2(C_2H_4OH)_2$
$[(CF_3)_2CF(CF_2)_6CH_2CH_2O]_2POONH_2(C_2H_4OH)_2$
$(C_8F_{17}CH_2CH_2O)_2POONH_2(C_2H_4OH)_2$
$(C_6F_{13}CH_2CH_2O)_2POONH_2(C_2H_4OH)_2$
$(C_{10}F_{21}CH_2CH_2O)_2POONH_2(C_2H_4OH)_2$
$(C_{12}F_{25}CH_2CH_2O)_2POONH_2(C_2H_4OH)_2$
$(C_{14}F_{29}CH_2CH_2O)_2POONH_2(C_2H_4OH)_2$
$(C_8F_{17}CH_2CH_2O)_2POONH_4$
$(C_8F_{17}CH_2CH_2O)_2POONH(C_2H_4OH)_3$
$[C_8F_{17}SO_2N(C_2H_5)CH_2CH_2O]_2POONH_4$
$[C_6F_{13}SO_2N(C_2H_5)CH_2CH_2O]_2POONH_4$
$[C_{10}F_{21}SO_2N(C_2H_5)CH_2CH_2O]_2POONH_4$
$[C_{12}F_{25}SO_2N(C_2H_5)CH_2CH_2O]_2POONH_4$
$[C_{14}F_{29}SO_2N(C_2H_5)CH_2CH_2O]_2POONH_4$
$[C_8F_{17}SO_2N(C_2H_5)CH_2CH_2O]_2POONH_2(CH_2CH_2OH)_2$
$[C_8F_{17}SO_2N(C_2H_5)CH_2CH_2O]_2POONH(CH_2CH_2OH)_3$
$[C_8F_{17}SO_2N(C_3H_7)CH_2CH_2O]_2POONH_2(CH_2CH_2OH)_2$
$[C_8F_{17}CON(C_2H_5)CH_2CH_2O]_2POONH(CH_2CH_2OH)_3$
$(C_8F_{17}COOCH_2CH_2O)_2POONH_4$
$(C_8F_{17}SO_2CH_2CH_2O)_2POONH_4$
$[C_8F_{17}(CH_2)_3OCH_2CH_2O]_2POONH_4$
$[C_8F_{17}CH_2CH(OH)CH_2O]_2POONH_4$

To prepare the di(fluoroalkyl containing group-substituted alkyl) phosphate salt of the formula (I), an alkyl ester of di(fluoroalkyl containing group-substituted alkyl) phosphate is hydrolyzed with a base. The alkyl ester of di(fluoroalkyl containing group-substituted alkyl) phosphate is preferably of the formula:

$$[R_f-A^1{}_k-(CH_2)_m-O]_2PO-OR \qquad (II)$$

wherein R is a secondary or tertiary alkyl or alkenyl group having 3 to 9 carbons, and $R_f$, $A^1$, k and m are the same as defined above. An alcoholic residue which is formed by the secondary or tertiary alkyl or alkenyl group is easily removed by hydrolysis to form the diester phosphate salt of the formula (I).

Specific examples of the alkyl ester of di(fluoroalkyl containing group-substituted alkyl) phosphate of the formula (II) are:

$(C_4F_9CH_2CH_2O)_2POOCH(CH_3)_2$
$[(CF_3)_2CF(CF_2)_6CH_2CH_2O]_2POOCH(CH_3)_2$
$(C_8F_{17}CH_2CH_2O)_2POOCH(CH_3)_2$
$(C_6F_{13}CH_2CH_2O)_2POOCH(CH_3)_2$
$(C_{10}F_{21}CH_2CH_2O)_2POOCH(CH_3)_2$
$(C_{12}F_{25}CH_2CH_2O)_2POOCH(CH_3)_2$
$(C_{14}F_{29}CH_2CH_2O)_2POOCH(CH_3)_2$
$(C_8F_{17}CH_2CH_2O)_2POOC(CH_3)_3$
$(C_8F_{17}CH_2CH_2O)_2POOCH_2CH_2CH(CH_3)_2$

[C$_8$F$_{17}$SO$_2$N(C$_2$H$_5$)CH$_2$CH$_2$O]$_2$POOCH(CH$_3$)$_2$
[C$_6$F$_{13}$SO$_2$N(C$_2$H$_5$)CH$_2$CH$_2$O]$_2$POOCH(CH$_3$)$_2$
[C$_{10}$F$_{21}$SO$_2$N(C$_2$H$_5$)CH$_2$CH$_2$O]$_2$POOCH(CH$_3$)$_2$
[C$_{12}$F$_{25}$SO$_2$N(C$_2$H$_5$)CH$_2$CH$_2$O]$_2$POOCH(CH$_3$)$_2$
[C$_{14}$F$_{29}$SO$_2$N(C$_2$H$_5$)CH$_2$CH$_2$O]$_2$POOCH(CH$_3$)$_2$
[C$_8$F$_{17}$SO$_2$N(C$_2$H$_5$)CH$_2$CH$_2$O]$_2$POOC(CH$_3$)$_3$
[C$_8$F$_{17}$SO$_2$N(C$_2$H$_5$)CH$_2$CH$_2$O]$_2$-POOCH$_2$CH$_2$CH(CH$_3$)$_2$
[C$_8$F$_{17}$SO$_2$N(C$_3$H$_7$)CH$_2$CH$_2$O]$_2$POOCH(CH$_3$)$_2$
[C$_8$F$_{17}$CON(C$_2$H$_5$)CH$_2$CH$_2$O]$_2$POOCH(CH$_3$)$_2$
[C$_8$F$_{17}$COOCH$_2$CH$_2$O]$_2$POOCH(CH$_3$)$_2$
[C$_8$F$_{17}$SO$_2$CH$_2$CH$_2$O]$_2$POOCH(CH$_3$)$_2$
[C$_8$F$_{17}$(CH$_2$)$_3$OCH$_2$CH$_2$O]$_2$POOCH$_2$CH(CH$_3$)$_2$
[C$_8$F$_{17}$CH$_2$CH(OH)CH$_2$O]$_2$POOCH(CH$_3$)$_2$

The base which is used to hydrolyze the alkyl ester of di(fluoroalkyl containing group-substituted alkyl) phosphate of the formula (II) is preferably an alkali hydroxide, an ammonium hydroxide or an amine. Examples of the alkali hydroxide are potassium hydroxide and sodium hydroxide. Examples of the amine are trimethylamine, triethylamine, tripropylamine, tributylamine, triethanolamine, diethylamine, dipropylamine, diethanolamine, ethylamine, propylamine and ethanolamine.

The hydrolysis can be carried out by adding ammonium hydroxide or an amine/water mixture, or an alkali hydroxide/alcohol/water mixture to the alkyl ester of di(fluoroalkyl containing group-substituted alkyl) phosphate. The alcohol which is used in hydrolysis includes a secondary or tertiary C$_3$–C$_6$ alcohol such as isopropyl alcohol, tert.-butyl alcohol, sec.-butyl alcohol, tert.-amyl alcohol, isoamyl alcohol and sec.-amyl alcohol.

The base is used in an amount of at least one equivalent, preferably 1 to 10 equivalents per mole of the alkyl di(fluoroalkyl containing group-substituted alkyl) phosphate.

The pressure during hydrolysis is not critical. Usually, the hydrolysis is carried out under an atmospheric pressure at a temperature of 80° to 100° C. for 2 to 6 hours.

The alkyl ester of di(fluoroalkyl containing group-substituted alkyl) phosphate of the formula (II) can be prepared by reacting a fluoroalkyl containing group-substituted alcohol of the formula:

$$R_f\text{—}A^1{}_k\text{—}(CH_2)_m\text{—}OH \qquad (III)$$

wherein $R_f$, $A^1$, k and m are the same as defined above, with a phosphoryl monoalkoxide dihalide of the formula:

$$RO\text{—}POX_2 \qquad (IV)$$

wherein each X is independently halogen atom, for example, chlorine or bromine and R is the same as defined above.

Specific examples of the alcohol of the formula (III) are:
C$_4$F$_9$CH$_2$CH$_2$OH
(CF$_3$)$_2$CF(CF$_2$)$_6$CH$_2$CH$_2$OH
C$_8$F$_{17}$CH$_2$CH$_2$OH
C$_{10}$F$_{21}$CH$_2$CH$_2$OH
C$_8$F$_{17}$SO$_2$N(C$_2$H$_5$)CH$_2$CH$_2$OH
C$_8$F$_{17}$SO$_2$N(C$_3$H$_7$)CH$_2$CH$_2$OH
C$_8$F$_{17}$SO$_2$N(CH$_3$)CH$_2$CH$_2$OH In the reaction, a molar ratio of the alcohol of the formula (III) to the phosphoryl monoalkoxide dihalide of the formula (IV) is preferably from 2:1 to 2:1.2. The reaction pressure is not critial. Usually, the reaction is carried out under an atmospheric pressure at 80° to 100° C. for 2 to 4 hours.

The phosphoryl monoalkoxide dihalide of the formula (IV) can be prepared by reacting a secondary or tertiary alcohol of the formula:

$$ROH \qquad (V)$$

wherein R is the same as defined above, with a phosphoryl trihalide of the formula:

$$POX_3 \qquad (VI)$$

wherein X is the same as defined above.

It is not preferable to use a primary alcohol instead of the secondary or tertiary alcohol of the formula (V), since the alkyl ester of di(fluoroalkyl containing group-substituted alkyl) phosphate of the formula (II) is hardly hydrolyzed.

As the phosphoryl trihalide of the formula (VI), usually phosphoryl trichloride is used because of its availability, although phosphoryl tribromide and phosphoryl bromide chloride may be used.

A molar ratio of the secondary or tertiary alcohol of the formula (V) to the phosphoryl trihalide of the formula (VI) is preferably about 1:1, preferably 0.9:1 to 1:1. The reaction pressure is not critical. Usually, the reaction is carried out under an atmospheric pressure at a temperature of room temperature (e.g. 20° C.) to 70° C. for 2 to 4 hours.

Therefore, the di(fluoroalkyl containing group-substituted alkyl) phosphate salt of the formula (I) can be prepared by reacting the secondary or tertiary alcohol of the formula (V) with the phosphoryl trihalide of the formula (VI) to produce the phosphoryl monoalkoxide dihalide of the formula (IV), reacting the phosphoryl monoalkoxide halide of the formula (IV) with the fluoroalkyl containing group-substituted alcohol of the formula (III) to produce the alkyl ester of di(fluoroalkyl containing group-substituted alkyl) phosphate of the formula (II), and hydrolyzing the alkyl ester of di(-fluoroalkyl containing group-substituted alkyl) phosphate of the formula (II) with the base.

According to the present invention, the di(fluoroalkyl containing group-substituted alkyl) phosphate salt can be prepared in a purity of not less than 90% by weight.

The present invention will be explained further in detail by the following Examples.

EXAMPLE 1

In a 200 ml flask equipped with a stirrer, a Dimroth condenser and a dropping funnel, phosphoryl trichloride (154 g, 1 mol) was charged and isopropyl alcohol (57 g, 0.95 mol) was dropwise added over 30 minutes with stirring. The reaction was exothermic and hydrogen chloride gas evolved. After completing the exothermic reaction, the reaction mixture was heated at 70° C. for one hour to give a colorless liquid mixture containing POCl$_3$ (1 g), C$_3$H$_7$OPOCl$_2$ (175 g) and (C$_3$H$_7$O)$_2$POCl (3 g).

In a one liter flask, a compound (200 g, 0.39 mol) of the formula:

$$C_nF_{n+1}CH_2CH_2OH$$

wherein molar fractions of compounds which have n of 8, 10, 12, 14 and 16 respectively are 55, 26, 12, 5 and 2, was charged. While a temperature was maintained at 80° C., the resultant liquid mixture (37 g) in the above was added with stirring. Hydrogen chloride evolved and the reaction started. The reaction mixture was heated to 95° C. and stirred for 2 hours. Then, water (1.5 g) was added and the reaction mixture was stirred for 2 hours to give a mixture of the following composition:

Diisopropyl mono(fluoroalkyl containing group-substituted alkyl) phosphate: 5% by weight Monoisopropyl di(fluoroalkyl containing group-substituted alkyl) phosphate: 93% by weight Tri(fluoroalkyl containing group-substituted phosphate: 2% by weight The mixture contained no ester having a chlorine atom.

Diethanolamine (65 g) as a hydrolyzing agent was added to the mixture. The mixture was stirred at 95° C. for 3 hours. After cooling, a wax-like solid was obtained. Yield: 297 g. The final product was analyzed by $^{31}$P-NMR spectrum to determine its composition. The result is shown in the Table.

EXAMPLE 2

A wax-like solid was obtained in the same manner as in Example 1 but using tert.-butyl alcohol (70.3 g, 0.95 mol) in place of isopropyl alcohol. Yield: 302 g. A composition of the final product is shown in the Table.

EXAMPLE 3

A wax-like solid was obtained in the same manner as in Example 1 but using tert.-amyl alcohol (83.6 g, 0.95 mol) in place of isopropyl alcohol. Yield: 315 g. A composition of the final product is shown in the Table.

EXAMPLE 4

An aqueous solution was obtained in the same manner as in Example 1 but using sodium hydroxide (20 g) and methyl alcohol (100 g) in place of diethanolamine. Yield: 352 g. A composition of the final product is shown in the Table.

EXAMPLE 5

A wax-like solid was obtained in the same manner as in Example 1 but using diethylamine (30 g) in place of diethanolamine. Yield: 262 g. A composition of the final product is shown in the Table.

EXAMPLE 6

In a 200 ml flask equipped with a stirrer, a Dimroth condenser and a dropping funnel, phosphoryl trichloride (154 g, 1 mol) was charged and isopropyl alcohol (57 g, 0.95 mol) was dropwise added over 30 minutes with stirring. The reaction was exothermic and hydrogen chloride gas evolved. After completing the exothermic reaction, the reaction mixture was heated at 70° C. for one hour to give a colorless liquid mixture containing POCl$_3$ (1 g), C$_3$H$_7$OPOCl$_2$ (175 g) and (C$_3$H$_7$O)$_2$POCl (3 g).

In a one liter flask, a compound (280 g, 0.39 mol) of the formula:

$$C_8F_{17}SO_2N(C_2H_5)CH_2CH_2OH$$

was charged. While a temperature was kept at 80° C., the resultant liquid mixture (37 g) in the above was added with stirring. Hydrogen chloride evolved and the reaction started. The reaction mixture was heated to 95° C. and stirred for 2 hours. Then, water (1.5 g) was added and the reaction mixture was stirred for 2 hours to give a mixture of the following composition:

Diisopropyl mono(fluoroalkyl containing group-substituted alkyl) phosphate: 4% by weight Monoisopropyl di(fluoroalkyl containing group-substituted alkyl) phosphate: 95% by weight Tri(fluoroalkyl containing group-substituted alkyl) phosphate: 1% by weight The mixture contained no ester having chlorine atom.

Diethanolamine (65 g) as a hydrolyzing agent was added to the mixture. The mixture was stirred at 95° C. for 3 hours. After cooling, a wax-like solid was obtained. Yield: 373 g. The final product was analyzed by $^{31}$P-NMR spectrum to determine its composition. The result is shown in the Table.

TABLE

| Example No. | Composition (% by weight) | | |
|---|---|---|---|
| | Monoester[1] | Diester[2] | Triester[3] |
| 1 | 5 | 93 | 2 |
| 2 | 4 | 92 | 4 |
| 3 | 5 | 92 | 3 |
| 4 | 5 | 95 | 0 |
| 5 | 3 | 92 | 5 |
| 6 | 4 | 95 | 1 |

Note:
[1]Monoester is a mono(fluoroalkyl containing group-substituted alkyl) phosphate salt.
[2]Diester is a di(fluoroalkyl containing group-substituted alkyl) phosphate salt which is a desired compound according to the present invention.
[3]Triester is a tri(fluoroalkyl containing group-substituted alkyl) phosphate.

In the above Examples, the di(fluoroalkyl containing group-substituted alkyl) phosphate salts are di(2-perfluoroalkyl-ethyl) phosphate salt and di(N-ethyl perfluoroalkanesulfonamidoethyl) phosphate salt. However, it is obvious for those skilled in the art to prepare other di(fluoroalkyl containing group-substituted alkyl) phosphate salts in the same manner as in the Examples. Although the Examples show the processes using diethanolamine, sodium hydroxide or diethylamine as the base, it is also obvious to use other bases since a hydrolysis reaction can be carried out with any base.

What is claimed is:

1. A process for preparing a di(fluoroalkyl containing group-substituted alkyl) phosphate salt of the formula:

$$[R_f\!-\!A^1{}_k\!-\!(CH_2)_m\!-\!O]_2PO\!-\!OA^2 \qquad (I)$$

which comprises hydrolyzing a mon-sec. or tert.-alkyl or alkenyl di(fluoroalkyl containing group-substituted alkyl) phosphate of the formula:

$$[R_f\!-\!A^1{}_k\!-\!(CH_2)_m\!-\!O]_2PO\!-\!OR \qquad (II)$$

with a base selected from the group consisting of an alkali hydroxide, an ammonium hydroxide and an amine, at a temperature of 80° to 100° C., the base being used in an amount of 1 to 10 equivalents per mole of the alkyl or alkenyl di(fluoroalkyl containing group-substituted alkyl) phosphate (II), wherein
each R$_f$ is independently a perfluoroalkyl group or ω-hydroperfluoroalkyl group having 3 to 21 carbon atoms and may be linear, branched, cyclic or a combination thereof,
each A$^1$ is independently a divalent group which is selected from the group consisting of —COO—, SO$_2$—, —O—, —(CH$_2$)$_3$—O—, —S—, —(CH$_2$-

)$_p$—NR'—, —CH$_2$CH(OR')—, —CO—NR'— or —SO$_2$—NR'—in which R' is a hydrogen or an alkyl group having 1 to 5 carbon atoms, and p is a integer of 1 to 6, A$^2$ is an alkaline metal or an ammonium group which may be substituted with an alkyl and/or hydroxyalkyl group, R is a secondary or tertiary alkyl or alkenyl group having 3 to 9 carbon atoms, k is 0 to 1, and m is an integer of 1 to 4.

2. The process of claim 1, wherein the di(fluoroalkyl containing group-substituted alkyl) phosphate salt of formula (I) is selected from the group consisting of:

(C$_4$F$_9$CH$_2$CH$_2$O)$_2$POONH$_2$(C$_2$H$_4$OH)$_2$
[(CF$_3$)$_2$CF(CF$_2$)$_6$CH$_2$CH$_2$O]$_2$POONH$_2$(C$_2$H$_4$OH)$_2$
(C$_8$F$_{17}$CH$_2$CH$_2$O)$_2$POONH$_2$(C$_2$H$_4$OH)$_2$
(C$_6$F$_{13}$CH$_2$CH$_2$O)$_2$POONH$_2$(C$_2$H$_4$OH)$_2$
(C$_{10}$F$_{21}$CH$_2$CH$_2$O)$_2$POONH$_2$(C$_2$H$_4$OH)$_2$
(C$_{12}$F$_{25}$CH$_2$CH$_2$O)$_2$POONH$_2$(C$_2$H$_4$OH)$_2$
(C$_{14}$F$_{29}$CH$_2$CH$_2$O)$_2$POONH$_2$(C$_2$H$_4$OH)$_2$
(C$_8$F$_{17}$CH$_2$CH$_2$O)$_2$POONH$_4$
(C$_8$F$_{17}$CH$_2$CH$_2$O)$_2$POONH(C$_2$H$_4$OH)$_3$
[C$_8$F$_{17}$SO$_2$N(C$_2$H$_5$)CH$_2$CH$_2$O]$_2$POONH$_4$
[C$_6$F$_{13}$SO$_2$N(C$_2$H$_5$)CH$_2$CH$_2$O]$_2$POONH$_4$
[C$_{10}$F$_{21}$SO$_2$N(C$_2$H$_5$)CH$_2$CH$_2$O]$_2$POONH$_4$
[C$_{12}$F$_{25}$SO$_2$N(C$_2$H$_5$)CH$_2$CH$_2$O]$_2$POONH$_4$
[C$_{14}$F$_{29}$SO$_2$N(C$_2$H$_5$)CH$_2$CH$_2$O]$_2$POONH$_4$
[C$_8$F$_{17}$SO$_2$N(C$_2$H$_5$)CH$_2$CH$_2$O]$_2$POONH$_2$(CH$_2$C-H$_2$OH)$_2$
[C$_8$F$_{17}$SO$_2$N(C$_2$H$_5$)CH$_2$CH$_2$O]$_2$POONH(CH$_2$C-H$_2$OH)$_3$
[C$_8$F$_{17}$SO$_2$N(C$_3$H$_7$)CH$_2$CH$_2$O]$_2$POONH(CH$_2$C-H$_2$OH)$_2$
[C$_8$F$_{17}$CON(C$_2$H$_5$)CH$_2$CH$_2$O]$_2$POONH(CH$_2$C-H$_2$OH)$_3$
(C$_8$F$_{17}$COOCH$_2$CH$_2$O)$_2$POONH$_4$
(C$_8$F$_{17}$SO$_2$CH$_2$CH$_2$O)$_2$POONH$_4$
[C$_8$F$_{17}$(CH$_2$)$_3$OCH$_2$CH$_2$O]$_2$POONH$_4$, and
[C$_8$F$_{17}$CH$_2$CH(OH)CH$_2$O]$_2$POONH$_4$.

3. The process of claim 1, wherein the alkyl ester of the di(fluoro-alkyl containing group substituted alkyl) phosphate of formula (II) is selected from the group consisting of:

(C$_4$F$_9$CH$_2$CH$_2$O)$_2$POOCH(CH$_3$)$_2$
[(CF$_3$)$_2$CF(CF$_2$)$_6$CH$_2$CH$_2$O]$_2$POOCH(CH$_3$)$_2$
(C$_8$F$_{17}$CH$_2$CH$_2$O)$_2$POOCH(CH$_3$)$_2$
(C$_6$F$_{13}$CH$_2$CH$_2$O)$_2$POOCH(CH$_3$)$_2$
(C$_{10}$F$_{21}$CH$_2$CH$_2$O)$_2$POOCH(CH$_3$)$_2$
(C$_{12}$F$_{25}$CH$_2$CH$_2$O)$_2$POOCH(CH$_3$)$_2$
(C$_{14}$F$_{29}$CH$_2$CH$_2$O)$_2$POOCH(CH$_3$)$_2$
(C$_8$F$_{17}$CH$_2$CH$_2$O)$_2$POOC(CH$_3$)$_3$
(C$_8$F$_{17}$CH$_2$CH$_2$O)$_2$POOCH$_2$CH$_2$CH(CH$_3$)$_2$
[C$_8$F$_{17}$SO$_2$N(C$_2$H$_5$)CH$_2$CH$_2$O]$_2$POOCH(CH$_3$)$_2$
[C$_6$F$_{13}$SO$_2$N(C$_2$H$_5$)CH$_2$CH$_2$O]$_2$POOCH(CH$_3$)$_2$
[C$_{10}$F$_{21}$SO$_2$N(C$_2$H$_5$)CH$_2$CH$_2$O]$_2$POOCH(CH$_3$)$_2$
[C$_{12}$F$_{25}$SO$_2$N(C$_2$H$_5$)CH$_2$CH$_2$O]$_2$POOCH(CH$_3$)$_2$
[C$_{14}$F$_{29}$SO$_2$N(C$_2$H$_5$)CH$_2$CH$_2$O]$_2$POOCH(CH$_3$)$_2$
[C$_8$F$_{17}$SO$_2$N(C$_2$H$_5$)CH$_2$CH$_2$O]$_2$POOCH(CH$_3$)$_3$
[C$_8$F$_{17}$SO$_2$N(C$_2$H$_5$)CH$_2$CH$_2$O]$_2$-POOCH$_2$CH$_2$CH(CH$_3$)$_2$
[C$_8$F$_{17}$SO$_2$N(C$_3$H$_7$)CH$_2$CH$_2$O]$_2$POOCH(CH$_3$)$_2$
[C$_8$F$_{17}$CON(C$_2$H$_5$)CH$_2$CH$_2$O]$_2$POOCH(CH$_3$)$_2$
[C$_8$F$_{17}$COOCH$_2$CH$_2$]$_2$POOCH(CH$_3$)$_2$
[C$_8$F$_{17}$SO$_2$CH$_2$CH$_2$O]$_2$POOCH(CH$_3$)$_2$
[C$_8$F$_{17}$(CH$_2$)OCH$_2$CH$_2$O]$_2$POOCH$_2$CH(CH$_3$)$_2$, and
[C$_8$F$_{17}$CH$_2$CH(OH)CH$_2$O]$_2$POOCH(CH$_3$)$_2$.

4. The process of claim 1, wherein the alkali hydroxide is selected from the group consisting of potassium hydroxide and sodium hydroxide.

5. The process of claim 1, wherein the amine is selected from the group consisting of trimethylamine, triethylamine, tripropylamine, tributylamine, triethanolamine, diethylamine, dipropylamine, diethanolamine, ethylamine, propylamine and ethanolamine.

6. The process of claim 4, wherein the alcohol of formula (III) is selected from the group consisting of:

C$_4$F$_9$CH$_2$CH$_2$OH
(CF$_3$)$_2$CF(CF$_2$)$_6$CH$_2$CH$_2$OH
C$_8$F$_{17}$CH$_2$CH$_2$OH
C$_{10}$F$_{21}$CH$_2$CH$_2$OH
C$_8$F$_{17}$SO$_2$N(C$_2$H$_5$)CH$_2$CH$_2$OH
C$_8$F$_{17}$SO$_2$N(C$_3$H$_7$)CH$_2$CH$_2$OH, and
C$_8$F$_{17}$SO$_2$N(CH$_3$)CH$_2$CH$_2$OH.

7. The process according to claim 4, wherein the molar ratio of the alcohol of formula (III) to the phosphoryl monoalkoxide dihalide of formula (IV) is 2:1 to 2:1.2.

8. The process of claim 1, wherein the base is selected from the group consisting of diethanolamine, sodium hydroxide and diethylamine.

9. A process for preparing a di(fluoroalkyl containing group-substituted alkyl) phosphate salt of formula (I)

$$[R_f\!-\!A^1{}_k\!-\!(CH_2)_m\!-\!O]_2PO\!-\!OA^2 \qquad (I)$$

which comprises:

reacting a secondary or tertiary alcohol with phosphoryl trihalide in a molar ratio of the secondary or tertiary alcohol to the phosphoryl trihalide of 0.9:1 to 1:1 at a temperature of room temperature to 70° C. to produce a phosphoryl monoalkoxide dihalide, reacting the phosphoryl monoalkoxide dihalide with a fluoroalkyl containing group-substituted alcohol in a molar ratio of said dihalide to the fluoroalkyl containing group-substituted alcohol of 1:2 to 1.2:2 at a temperature of 80° to 100° C. to produce a mono sec.- or tert.-alkyl di(fluoroalkyl containing group-substituted alkyl) phosphate of formula (II)

$$[R_f\!-\!A^1{}_k\!-\!(CH_2)_m\!-\!O]_2PO\!-\!OR \qquad (II)$$

and hydrolyzing the mono-sec.- or tert.-alkyl di(fluoroalkyl containing group-substituted alkyl) phosphate of formula (II) with a base at a temperature of 80° to 100° C., the base being used in an amount of 1 to 10 equivalent per mole of the alkyl or alkenyl di(fluoroalkyl containing group-substituted alkyl) phosphate of formula (II), wherein each R$_f$ is independently a perfluoroalkyl group or ω-hydroperfluoroalkyl group having 3 to 21 carbon atoms and may be linear, branched, cyclic or a combination thereof, each A$^1$ is independently a divalent group which is selected from the group consisting of —COO—, SO$_2$—, —O—, —(CH$_2$)$_3$—O—, —S—, —(CH$_2$)$_p$—NR'—, —CH$_2$CH(OR')—, —CO—NR'— or —SO$_2$—NR'— in which R' is a hydrogen or an alkyl group having 1 to 5 carbon atoms, and p is a integer of 1 to 6, $A^2$ is an alkaline metal or an ammonium group which may be substituted with an alkyl and/or hydroxyalkyl group, R is a secondary or tertiary alkyl or alkenyl group having 3 to 9 carbon atoms, k is 0 to 1, and m is an integer of 1 to 4.

10. A process for preparing a di(fluoroalkyl containing group-substituted alkyl) phosphate salt of the formula:

$$[R_f-A^1{}_k-(CH_2)_m-O]_2PO-OA^2 \qquad (I)$$

which comprises reacting a secondary or tertiary alcohol of the formula:

$$ROH \qquad (V)$$

with a phosphoryl trihalide of the formula:

$$POX_3 \qquad (VI)$$

in a molar ratio of the secondary or tertiary alcohol to the phosphoryl trihalide of 0.9:1 to 1:1 at a temperature of room temperature to 70° C. to produce a phosphoryl monoalkoxide dihalide of the formula:

$$RO-POX_2 \qquad (IV)$$

and reacting the phosphoryl monoalkoxide dihalide of the formula (IV) with a fluoroalkyl containing group-substituted alcohol of the formula:

$$R_f-A^1{}_k-(CH_2)_m-OH \qquad (III)$$

in a molar ratio of said dihalide to the fluoroalkyl containing group-substituted alcohol of 1:2 to 1.2:2 at a temperature of 80° to 100° C. to produce an alkyl ester of di(fluoroalkyl containing group-substituted alkyl) phosphate of the formula:

$$[R_f-A^1{}_k-(CH_2)_m-O]_2PO-OR \qquad (II)$$

and then hydrolyzing the alkyl ester of di(fluoroalkyl containing group-substituted alkyl) phosphate of the formula (II) with a base selected from the group consisting of an alkali hydroxide, an ammonium hydroxide and an amine, at a temperature of 80° to 100° C., the base being used in an amount of 1 to 10 equivalent per mole of the alkyl or alkenyl di(fluoroalkyl containing group-substituted alkyl) phosphate of formula (II), wherein each $R_f$ is independently a perfluoroalkyl group or ω-hydroperfluoroalkyl group having 3 to 21 carbon atoms, each $A^1$ is independently a divalent group which is selected from the group consisting of —COO—, $SO_2$—, —O—, —$(CH_2)_3$—O—, —S—, —$(CH_2)_p$—NR'—, —$CH_2CH(OR')$—, —CO—NR'— or —$SO_2$—NR'— in which R' is a hydrogen or an alkyl group having 1 to 5 carbon atoms, and p is a integer of 1 to 6, $A^2$ is an alkaline metal or an ammonium group which optionally have an alkyl and/or hydroxyalkyl substituent, R is a secondary or tertiary alkyl or alkenyl group having 3 to 9 carbons, each X is independently halogen, k is 0 to 1, and m is an integer of 1 to 4.

* * * * *